United States Patent
Song et al.

(10) Patent No.: US 10,994,416 B2
(45) Date of Patent: May 4, 2021

(54) METHOD FOR CONTROLLING A LIMB MOTION INTENTION UNDERSTANDING AND UPPER LIMB REHABILITATION TRAINING ROBOT BASED ON FORCE SENSE INFORMATION AND POSTURE INFORMATION

(71) Applicant: SOUTHEAST UNIVERSITY, Nanjing (CN)

(72) Inventors: Aiguo Song, Nanjing (CN); Ke Shi, Nanjing (CN); Xinyu Tang, Nanjing (CN); Huijun Li, Nanjing (CN); Baoguo Xu, Nanjing (CN); Hong Zeng, Nanjing (CN)

(73) Assignee: SOUTHEAST UNIVERSITY, Nanjing (CN)

(*) Notice: Subject to any disclaimer, the term of this patent is extended or adjusted under 35 U.S.C. 154(b) by 0 days.

(21) Appl. No.: 16/954,207

(22) PCT Filed: May 23, 2018

(86) PCT No.: PCT/CN2018/088080
§ 371 (c)(1),
(2) Date: Jun. 16, 2020

(87) PCT Pub. No.: WO2019/119724
PCT Pub. Date: Jun. 27, 2019

(65) Prior Publication Data
US 2021/0086356 A1    Mar. 25, 2021

(30) Foreign Application Priority Data

Dec. 21, 2017  (CN) .......................... 201711395042.X

(51) Int. Cl.
*G06F 17/00* (2019.01)
*B25J 9/16* (2006.01)
(Continued)

(52) U.S. Cl.
CPC ............. *B25J 9/163* (2013.01); *A61B 5/1114* (2013.01); *A61B 5/1116* (2013.01);
(Continued)

(58) Field of Classification Search
CPC . B25J 9/163; B25J 13/088; B25J 13/02; B25J 13/085; B25J 9/1694; A61B 5/1116;
(Continued)

(56) References Cited

U.S. PATENT DOCUMENTS 6,162,189 A * 12/2000 Girone .................... G16H 20/30
                                                    600/592
7,390,309 B2 * 6/2008 Dariush .................... A61H 1/00
                                                    601/35
(Continued)

FOREIGN PATENT DOCUMENTS

| CN | 100998536 A | 7/2007 |
| CN | 101301250 A | 11/2008 |

(Continued)

OTHER PUBLICATIONS

Wu Changcheng, et al., Upper limb rehabilitation training robot and its control method, Chinese Journal of Scientific Instrument, May 2014, vol. 35, No. 5.

*Primary Examiner* — Ronnie M Mancho
(74) *Attorney, Agent, or Firm* — Bayramoglu Law Offices LLC

(57) ABSTRACT

A method for controlling a limb motion intention recognizing and rehabilitation training robot based on force sense information includes: acquiring data of a three-dimensional force and a three-dimensional moment by a six-dimensional force sensor held in a hand; calculating forces and moments produced by a palm, a forearm and an upper arm of a human body according to a constructed human arm model to achieve recognition of limb motion intention; fixing the (Continued)

six-dimensional force sensor on a rocker at an end of the three-degree-of-freedom upper limb rehabilitation training robot, acquiring motion intention of an arm of the human body according to the motion intention recognition method, and controlling the rehabilitation training robot to achieve auxiliary active training under a weak active force.

1 Claim, 4 Drawing Sheets

(51) Int. Cl.
| | |
|---|---|
| A61B 5/11 | (2006.01) |
| B25J 13/08 | (2006.01) |
| B25J 13/02 | (2006.01) |
| G05B 19/4155 | (2006.01) |
| G16H 20/30 | (2018.01) |
| G16H 40/63 | (2018.01) |
| A61B 90/00 | (2016.01) |

(52) U.S. Cl.
CPC .............. *B25J 9/1694* (2013.01); *B25J 13/02* (2013.01); *B25J 13/085* (2013.01); *B25J 13/088* (2013.01); *G05B 19/4155* (2013.01); *G16H 20/30* (2018.01); *G16H 40/63* (2018.01); *A61B 2090/064* (2016.02); *A61B 2505/09* (2013.01); *G05B 2219/45109* (2013.01)

(58) Field of Classification Search
CPC .............. A61B 5/1114; A61B 2505/09; A61B 2090/064; G16H 40/63; G16H 20/30; G05B 19/4155; G05B 2219/45109
USPC ........................................................ 700/246
See application file for complete search history.

(56) References Cited

U.S. PATENT DOCUMENTS

| | | | | |
|---|---|---|---|---|
| 7,725,175 | B2* | 5/2010 | Koeneman | A61N 1/36003 600/546 |
| 9,161,817 | B2* | 10/2015 | Olson | A61B 34/77 |
| 9,693,883 | B2* | 7/2017 | Herr | A61F 2/68 |
| 2005/0043718 | A1* | 2/2005 | Madhani | A61B 34/77 606/1 |
| 2006/0106369 | A1* | 5/2006 | Desai | A61B 34/76 606/1 |
| 2006/0142657 | A1* | 6/2006 | Quaid | A61B 17/1703 600/424 |
| 2007/0016329 | A1* | 1/2007 | Herr | A61F 2/70 700/250 |
| 2007/0171199 | A1* | 7/2007 | Gosselin | A61H 3/008 345/156 |
| 2007/0179534 | A1* | 8/2007 | Firlik | A61B 5/18 607/3 |
| 2011/0043537 | A1* | 2/2011 | Dellon | G09B 23/28 345/647 |
| 2012/0143374 | A1* | 6/2012 | Mistry | B62D 57/032 700/259 |
| 2012/0330198 | A1* | 12/2012 | Patoglu | B25J 9/0006 601/33 |
| 2013/0310977 | A1* | 11/2013 | Tsusaka | B25J 9/163 700/257 |
| 2013/0310979 | A1* | 11/2013 | Herr | B62D 57/032 700/258 |
| 2016/0005338 | A1* | 1/2016 | Melendez-Calderon | G09B 23/32 434/267 |
| 2016/0051433 | A1* | 2/2016 | Patoglu | B25J 9/1694 606/130 |
| 2016/0221189 | A1* | 8/2016 | Nilsson | B25J 9/1653 |
| 2017/0027803 | A1* | 2/2017 | Agrawal | A61B 5/224 |
| 2017/0042717 | A1* | 2/2017 | Agrawal | A61F 5/024 |
| 2017/0086932 | A1* | 3/2017 | Auld | A61B 34/71 |
| 2017/0188992 | A1* | 7/2017 | O'Brien | G16H 50/30 |
| 2017/0231787 | A1* | 8/2017 | Noda | B25J 13/085 623/26 |
| 2019/0307583 | A1* | 10/2019 | Herr | A61F 2/64 |
| 2019/0328604 | A1* | 10/2019 | Contreras-Vidal | A61F 5/0123 |
| 2020/0085603 | A1* | 3/2020 | Gregg | A61F 5/0102 |
| 2020/0298403 | A1* | 9/2020 | Nilsson | G05B 19/401 |
| 2020/0315895 | A1* | 10/2020 | Song | A61H 1/0262 |

FOREIGN PATENT DOCUMENTS

| | | |
|---|---|---|
| CN | 101533578 A | 9/2009 |
| CN | 105437209 A | 3/2016 |
| KR | 10694369 A1 | 1/2017 |

* cited by examiner

METHOD FOR CONTROLLING A LIMB MOTION INTENTION UNDERSTANDING AND UPPER LIMB REHABILITATION TRAINING ROBOT BASED ON FORCE SENSE INFORMATION AND POSTURE INFORMATION

CROSS REFERENCE TO THE RELATED APPLICATIONS

This application is the national phase entry of International Application No. PCT/CN2018/088080, filed on May 23, 2018, which is based upon and claims priority to Chinese Patent Application No. 201711395042.X, filed on Dec. 21, 2017, the entire contents of which are incorporated herein by reference.

TECHNICAL FIELD

The present invention relates to a method for controlling a limb motion intention understanding and upper limb rehabilitation training robot base on force sense information and posture information, which is used for rehabilitation training robot assisted rehabilitation training and belongs to a robot control method.

BACKGROUND

With the current rapid development of robot technology, human-machine interaction is an important direction. The robots cooperate with humans to complete tasks, so that humans and robots can develop their respective strengths. Therefore, how to achieve friendly interaction between humans and robots has become an important issue. Especially in the field of rehabilitation training robots, studies have shown that proper active rehabilitation can make patients achieve better rehabilitation results. However, the patients often cannot control their limb motions freely like healthy people due to the decline of the physical motion function, and therefore they need to perform active training with the assistance of robots. At this time, the robot needs to accurately recognize the motion intention of the patient and make a corresponding response. The traditional motion intention recognition generally uses electromyography signal or electroencephalogram signal, but it is inconvenient to wear and the signals are unstable. Therefore, it is of great value to develop a motion intention recognition method that is easy to use and has stable signals, and perform motion control of rehabilitation robots.

SUMMARY

An objective of the present invention is to provide a method for controlling a limb motion intention understanding and upper limb rehabilitation training robot based on force sense information and posture information.

The objective of the present invention is achieved by the following. The method includes: detecting human body motion intention by a six-dimensional force sensor, detecting a posture of an arm of a human body by three posture sensors respectively fixed on a palm, a forearm and an upper arm of the human body, inputting human body motion intention information and posture information of the arm to a controller of the rehabilitation training robot, and processing the input information by the controller according to a human body motion intention recognition model based on force sense information, and controlling the rehabilitation training robot by the controller to make corresponding actions. Firstly, one end of the six-dimensional force sensor is fixed on an end of the robot, and the other end of the six-dimensional force sensor is fixed on a rocker, the palm of the human body holds the rocker, the forearm is fixed on a supporting arm of the three-degree-of-freedom upper limb rehabilitation training robot through a strap, and the palm, the forearm and the upper arm wear posture detection modules, respectively. During use, the arm of the human body is in a certain state, the posture sensors acquire information of the state and input the information of the state to the controller. The arm of the human body exerts a force acting on the six-dimensional force sensor through the rocker, the force sensor inputs a corresponding signal to the controller; and the controller solves acquired posture parameters and force sense parameters through the established intention recognition model, and controls the rehabilitation training robot to make corresponding actions. Specifically, the intention recognition model is as follows:

a) the arm of the human body is equivalent to a mechanical arm with three connecting rods connected in series, wherein the palm, the forearm and the upper arm are a connecting rod $U_0L_0$, a connecting rod $L_0H_0$, and a connecting rod $H_0S_0$, respectively; the palm and the sensor are relatively stationary, and the remaining portion of the human body except the arm is equivalent to a base Base in a stationary state;

b) a coordinate system of each joint is established, the arm of the human body naturally hangs down against a torso; for a coordinate system of a shoulder joint, a center point $U_O$ of a connection between the upper arm and the torso is an origin, and a downward direction along an axis of the arm is the positive direction of a $U_X$ axis, an outward direction perpendicular to the front side of the human body is the positive direction of a $U_Z$ axis, and a direction pointing to the torso perpendicular to a $U_XU_Z$ plane is the positive direction of a $U_Y$ axis; and similarly, coordinate systems of an elbow joint and a wrist joint are established; a basic coordinate system is established, wherein, a connection between the upper arm and the torso is an origin, an outward direction perpendicular to a human body plane is the positive direction of a $B_X$ axis, a vertically upward direction is the positive direction of a $B_Z$ axis, and a direction pointing to the torso perpendicular to a $B_XB_Z$ plane is the positive direction of a $B_Y$ axis; the six-dimensional force sensor and the palm of the human body are relatively stationary, and a point of the six-dimensional force sensor contact with the palm is an origin $S_O$, and directions of three axes are the same as above;

c) $_B^AT_f$ is defined as a conversion matrix of force parameters from a B coordinate system to an A coordinate system, $^AF_B$ is a representation in the A coordinate system of a force vector F in the B coordinate system, $^AP_{BORG}$ is a representation in the A coordinate system of the origin of the B coordinate system, $_B^AR$ is a rotation matrix from the B coordinate system to the A coordinate system, $^AJ$ is a Jacobian matrix relative to the A coordinate system, and $\tau$ is a moment vector of the joint; force sense data obtained by the sensor is a six-dimensional vector $^SF_S$ containing a three-dimensional force and a three-dimensional moment; $_B^AT_f$ is a 6×6 matrix and is expressed as follows:

$$_B^AT_f = \begin{bmatrix} _B^AR & 0 \\ ^AP_{BORG} \times _B^AR & _B^AR \end{bmatrix};$$

d) the following can be obtained:

$${}^B F_B = {}^B_U T \times {}^U_L T \times {}^H_S T \times {}^S F_S,$$

$$\tau = {}^B J^T \times {}^B F_B,$$

wherein, ${}^S F_S$ can be detected by the sensor and is expressed as ${}^B F_B$ in the basic coordinate system, and $\tau$ is a moment vector of each joint;

e) the posture of the human body is detected through the three posture sensors installed on the palm, the forearm and the upper arm, on this basis, angles between connecting rods required in the model are calculated, and the moment vector $\tau$ of each joint of the human body is finally obtained by the controller according to the model in a) to d).

The controller controls the three-degree-of-freedom upper limb rehabilitation training robot to make corresponding motions through the acquired moment vector $\tau$ of each joint of the arm of the human body, and an upper arm connecting rod and a forearm connecting rod of the robot respond to rotation motion intentions of the shoulder joint and the elbow joint of the human body on the $B_X B_Y$ plane, respectively; and the rocker of the robot mainly responds to a rotation motion intention of the wrist joint on the $B_Y B_Z$ plane. An output signal of the force sensor comprises six-dimensional force data containing the three-dimensional force and the three-dimensional moment, wherein a force and a moment signal perpendicular to a motion plane are used to turn on/off the rehabilitation training robot by a patient, when the palm of the patient acts on the rocker, a force and a moment are generated accordingly, and then the robot is turned on; and when the robot needs to be turned off, the patient only needs to release the palm to stop the robot.

Compared with the prior art, the present invention has the following advantages:

1. The signal of the force sensor is stable and is convenient to acquire and process, and the output data of the six-dimensional force sensor is rich in information, which is convenient for better recognition of human body motion intention.

2. The force sensor is fixed on the end of the robot. It has a small volume, is easy to install, and has good transplantability. It can be easily installed on any rehabilitation training robot, meaning that the model is easy to transplant to other robots for use.

3. The intention recognition model can be extended to an upper limb rehabilitation training robot with more degrees of freedom (which can be exactly the same as the degrees of freedom of human arms) to better assist the patients in rehabilitation training.

4. The force sensor has high precision and can sense small forces and moments, and for the patients in the early stage of rehabilitation training, the force sensor can better sense their motion intentions, and will not fail due to the weak signal.

5. The rehabilitation training robot is controlled by the motion intention recognition method, and thus the patient can use a tiny force to control the rehabilitation robot with a larger joint motor reduction ratio to assist himself in completing the rehabilitation training, improving the participation in the training process, and the safety and comfort of the patient in the rehabilitation training can also be better ensured through his own control.

DETAILED DESCRIPTION OF THE EMBODIMENTS

Figure 1:
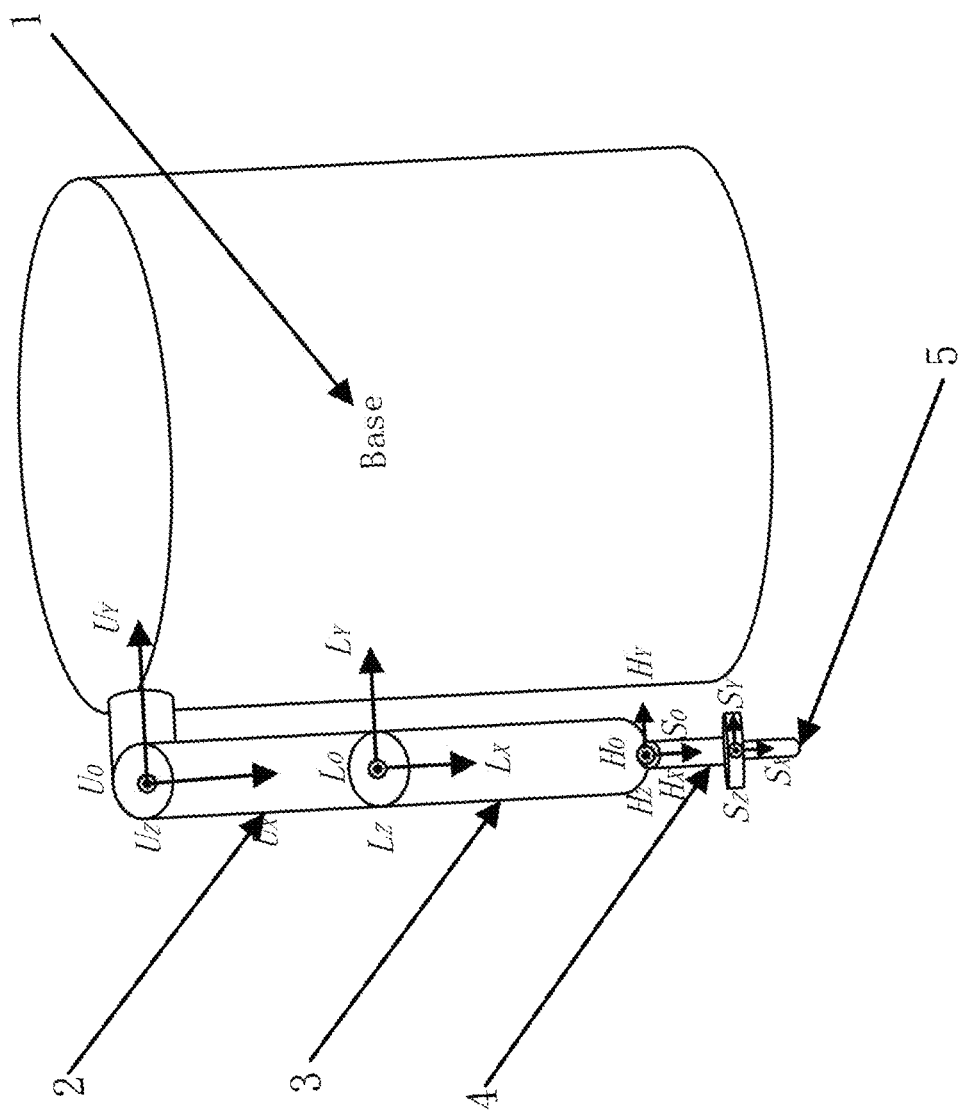
FIG. 1 is an assembly diagram of a unilateral mechanism of an upper limb rehabilitation training mechanism according to the present invention.
Figure 2:
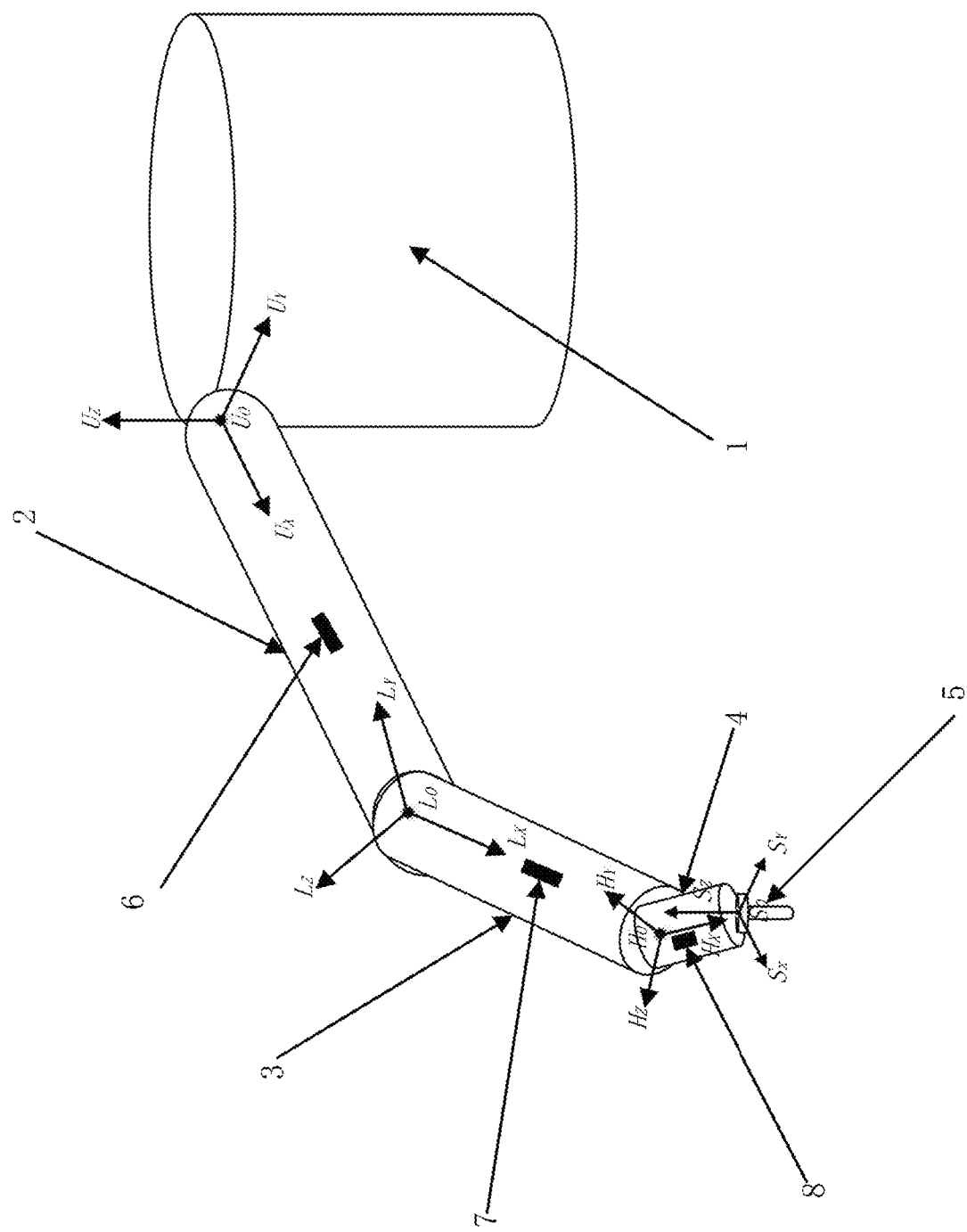
FIG. 2 is an overall assembly diagram of the upper limb rehabilitation training mechanism according to the present invention.
Figure 3:
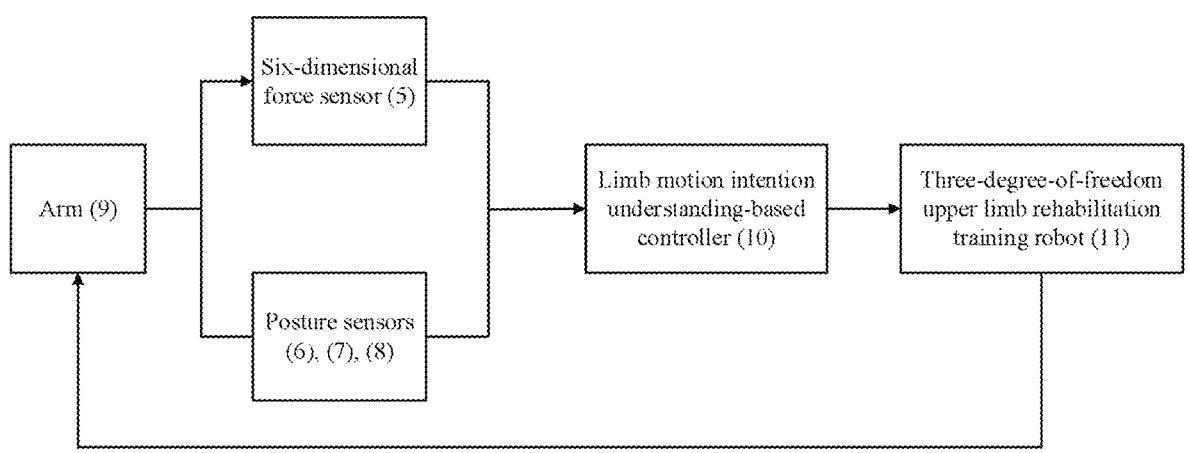
FIG. 3 is a partial diagram of an installation position of a force sensor of the upper limb rehabilitation training mechanism according to the present invention.
Figure 4:
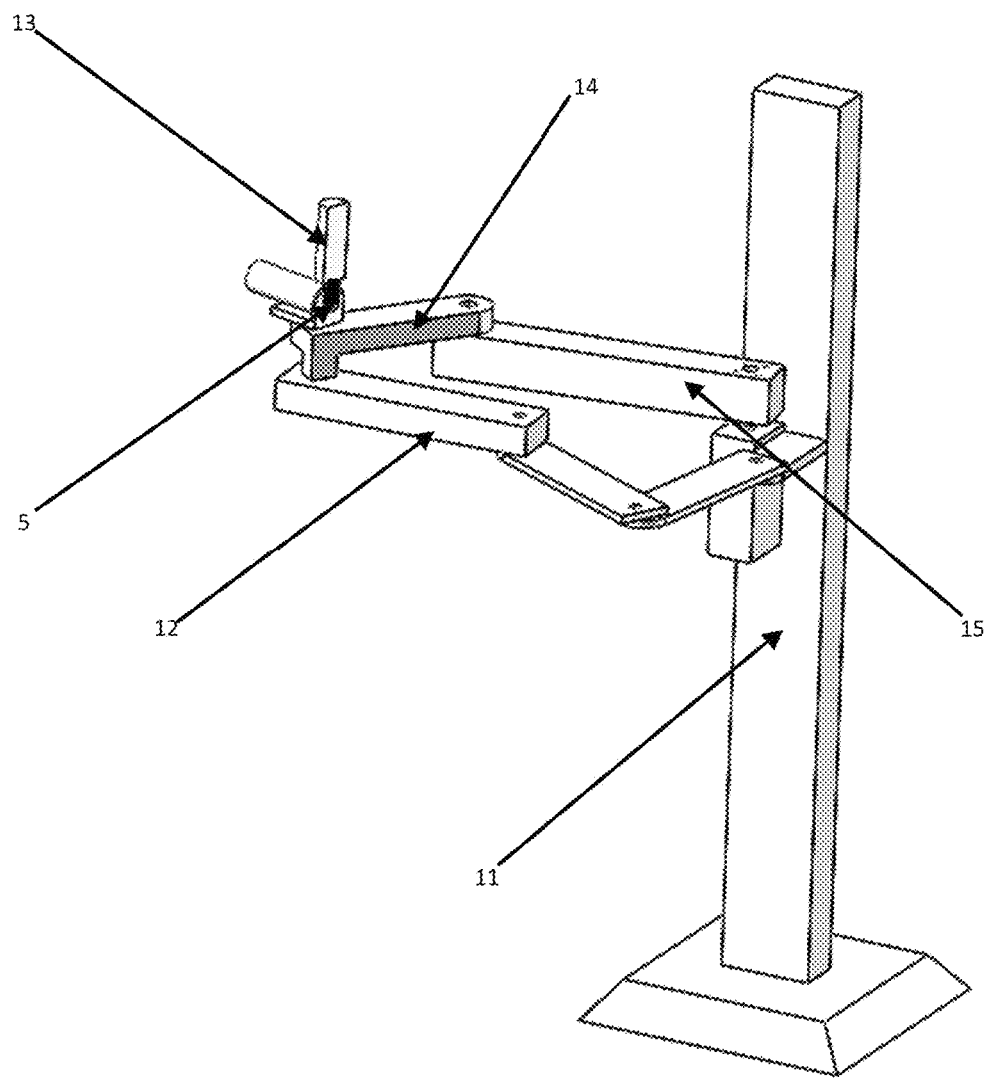
FIG. 4 is a partial diagram of a shaft fit of the upper limb rehabilitation training mechanism according to the present invention.

The human body motion intention is detected by means of a six-dimensional force sensor. Three posture sensors respectively fixed on a palm, a forearm and an upper arm of a human body are adopted to detect the posture of an arm of the human body, and human body motion intention information and posture information of the arm are input to a controller of a rehabilitation training robot. The controller processes the input information according to a human body motion intention recognition model based on force sense information, and controls the rehabilitation training robot to make corresponding actions. First, one end of the six-dimensional force sensor is fixed on an end of the robot, and the other end of the six-dimensional force sensor is fixed on a rocker. The palm of the human body holds the rocker, the forearm is fixed on a supporting arm of the three-degree-of-freedom upper limb rehabilitation training robot through a strap, and the palm, the forearm and the upper arm wear posture detection modules, respectively. During use, the arm of the human body is in a certain state, the posture sensors acquire information of the state and input the information of the state to the controller, the arm of the human body exerts a force acting on the six-dimensional force sensor through the rocker, and the force sensor inputs a corresponding signal to the controller, and the controller solves the acquired posture parameters and force sense parameters by means of the established intention recognition model, and controls the rehabilitation training robot to make corresponding actions. The intention recognition model is established as follows.

a) The arm of the human body is equivalent to a mechanical arm with three connecting rods connected in series, wherein the palm, the forearm and the upper arm are the connecting rod $U_0 L_0$, the connecting rod $L_0 H_0$, and the connecting rod $H_0 S_0$, respectively. The palm and the sensor are relatively stationary, and the remaining portion of the human body except the arm is equivalent to a base Base in a stationary state.

b) A coordinate system of each joint is established, the arm of the human body naturally hangs down against a torso. For a coordinate system of the shoulder joint, a center point $U_O$ of a connection between the upper arm and the torso is the origin, and a downward direction along an axis of the arm is the positive direction of a $U_X$ axis, an outward direction perpendicular to the front side of the human body is the positive direction of a $U_Z$ axis, and a direction pointing to the torso perpendicular to the $U_X U_Z$ plane is the positive direction of a $U_Y$ axis; and similarly, coordinate systems of the elbow joint and the wrist joint are established. A basic coordinate system is established, wherein, the connection between the upper arm and the torso is the origin, an outward direction perpendicular to the human body plane is the positive direction of a $B_X$ axis, a vertically upward direction is the positive direction of a $B_Z$ axis, and a direction pointing to the torso perpendicular to the $B_X B_Z$ plane is the positive direction of a $B_Y$ axis. The six-dimensional force sensor and the palm of the human body are relatively stationary, and the point of the six-dimensional force sensor contact with the palm is the origin $S_O$, and directions of three axes are the same as above.

c) $_B^A T_f$ is defined as a conversion matrix of force parameters from a B coordinate system to an A coordinate system, $^A F_B$ is a representation in the A coordinate system of a force vector F in the B coordinate system, $^A P_{BORG}$ is a representation in the A coordinate system of the origin of the B coordinate system, $_B^A R$ is a rotation matrix from the B coordinate system to the A coordinate system, $^A J$ is a Jacobian matrix relative to the A coordinate system, and $\tau$ is a moment vector of the joint. Force sense data obtained by the sensor is a six-dimensional vector $^S F_S$ containing a three-dimensional force and a three-dimensional moment. $_B^A T_f$ is a 6×6 matrix and is expressed as follows:

$$_B^A T_f = \begin{bmatrix} _B^A R & 0 \\ ^A P_{BORG} \times _B^A R & _B^A R \end{bmatrix}.$$

d) The following can be obtained:

$$^B F_B = _U^B T_f \times _L^U T_f \times _S^H T_f \times ^S F_S,$$

$$\tau = ^B J^T \times ^B F_B,$$

wherein, $^S F_S$ can be detected by the sensor and is expressed as $^B F_B$ in the basic coordinate system, and is a moment vector of each joint.

e) The posture of the human body is detected through the three posture sensors installed on the palm, the forearm and the upper arm, on this basis, angles between connecting rods required in the model are calculated, and the moment vector $\tau$ of each joint of the human body is finally obtained by the controller according to the model in a) to d).

The controller controls the three-degree-of-freedom upper limb rehabilitation robot to make corresponding motions through the acquired moment vector $\tau$ of each joint of the arm of the human body, and an upper arm connecting rod and a forearm connecting rod of the robot respond to the rotation motion intentions of the shoulder joint and the elbow joint of the human body on the $B_X B_Y$ plane, respectively; and the rocker of the robot mainly responds to the rotation motion intention of the wrist joint on the $B_Y B_Z$ plane. An output signal of the force sensor includes six-dimensional force data containing the three-dimensional force and the three-dimensional moment, wherein a force and a moment signal which are perpendicular to a motion plane are used to turn on/off the rehabilitation training robot by a patient, when the palm of the patient acts on the rocker, a force and a moment are generated accordingly, and then the robot is turned on; and when the robot needs to be turned off, the patient only needs to release the palm to stop the robot.

What is claimed is:

1. A method for controlling a limb motion intention understanding and upper limb rehabilitation training robot based on force sense information and posture information, wherein a limb motion intention recognition model is adopted in the method based on the force sense information and a three-degree-of-freedom upper limb rehabilitation training robot is controlled in the method based on the limb motion intention recognition model, comprising the following steps:

detecting human body motion intention information by a six-dimensional force sensor, detecting posture information of an arm of a human body by three posture sensors, wherein the three posture sensors are fixed on a palm, a forearm and an upper arm of the human body, respectively;

inputting the human body motion intention information and the posture information of the arm to a controller of the three-degree-of-freedom upper limb rehabilitation training robot;

processing the human body motion intention information and the posture information by the controller according to the limb motion intention recognition model; and controlling the three-degree-of-freedom upper limb rehabilitation training robot by the controller to make actions corresponding to the human body motion intention information and the posture information;

wherein, a first end of the six-dimensional force sensor is fixed on an end of the robot, and a second end of the six-dimensional force sensor is fixed on a rocker, the palm of the human body holds the rocker, the forearm is fixed on a supporting arm of the three-degree-of-freedom upper limb rehabilitation training robot through a strap, and the palm, the forearm and the upper arm wear posture sensors, respectively; during use, the posture sensors acquire the posture information of the arm of the human body and input the posture information to the controller; the arm of the human body exerts a force acting on the six-dimensional force sensor through the rocker, the six-dimensional force sensor inputs a signal corresponding to the force to the controller; and the controller solves acquired posture parameters and force sense parameters through the limb motion intention recognition model, and the controller controls the rehabilitation training robot to make actions corresponding to the acquired posture parameters and force sense parameters; wherein the limb motion intention recognition model is established as follows:

step (a): the arm of the human body is equivalent to a mechanical arm with three connecting rods connected in series, wherein the palm is a first connecting rod $U_0 L_0$ of the three connecting rods, the forearm is a second connecting rod $L_0 H_0$ of the three connecting rods, and the upper arm is a third connecting rod $H_0 S_0$ of the three connecting rods; the palm and the six-dimensional force sensor are relatively stationary, and a remaining portion of the human body except the arm is equivalent to a base in a stationary state;

step (b): a coordinate system of each joint of a shoulder joint, an elbow joint and a wrist joint is established, the arm of the human body naturally hangs down against a torso; in a coordinate system of the shoulder joint, a center point $U_O$ of a connection between the upper arm and the torso is an origin of the coordinate system of the shoulder joint, and a downward direction along an axis of the arm is a positive direction of a $U_X$ axis, an outward direction perpendicular to a front side of the human body is a positive direction of a $U_Z$ axis, and a direction pointing to the torso perpendicular to a $U_X U_Z$ plane is a positive direction of a $U_Y$ axis; and similarly, coordinate systems of the elbow joint and the wrist joint are established; a basic coordinate system is established, wherein, a connection between the upper arm and the torso is an origin of the basic coordinate system, an outward direction perpendicular to the front side of the human body is a positive direction of a $B_X$ axis, a vertically upward direction is a positive direction of a $B_Z$ axis, and a direction pointing to the torso perpendicular to a $B_X B_Z$ plane is a positive direction of a $B_Y$ axis; the six-dimensional force sensor and the palm of the human body are relatively stationary, and a point of the six-dimensional force sensor contact with the palm is an origin $S_O$ of a coordinate system of the six-dimensional force sensor, and directions of three axes of the coordinate system of the six-dimensional force sensor are the same as the basic coordinate system;

step (c): $^A_B T_f$ is defined as a conversion matrix of force parameters from a B coordinate system to an A coordinate system, $^A F_B$ is a representation in the A coordinate system of a force vector F in the B coordinate system, $^A P_{BORG}$ is a representation in the A coordinate system of an origin of the B coordinate system, $^A_B R$ is a rotation matrix from the B coordinate system to the A coordinate system, $^A J$ is a Jacobian matrix relative to the A coordinate system, and $\tau$ is a moment vector of the each joint; force sense data obtained by the six-dimensional force sensor is a six-dimensional vector $^S F_S$ containing a three-dimensional force and a three-dimensional moment; $^A_B T_f$ is a 6×6 matrix and is expressed as follows:

$$^A_B T_f = \begin{bmatrix} ^A_B R & 0 \\ ^A P_{BORG} \times ^A_B R & ^A_B R \end{bmatrix};$$

step (d): the following is obtained:
$^B F_B = ^B_U T_f \times ^U_L T_f \times ^L_H T_f \times ^S F_S$, $\tau = ^A J^T \times ^B F_B$, wherein, $^S F_S$ is detected by the six-dimensional force sensor and is expressed as $^B F_B$ in the basic coordinate system, and $\tau$ is the moment vector of the each joint; and step (e): the posture information of the arm of the human body is detected through the three posture sensors installed on the palm, the forearm and the upper arm, wherein angles between the three connecting rods required in the limb motion intention recognition model are calculated based on the posture information, and the moment vector $\tau$ of each joint of the human body is finally obtained by the controller according to the limb motion intention recognition model in steps (a) to (d);

wherein, the controller controls the three-degree-of-freedom upper limb rehabilitation training robot to make motions through the moment vector $\tau$ of the each joint of the arm of the human body, and an upper arm connecting rod of the three-degree-of-freedom upper limb rehabilitation training robot responds to a rotation motion intention of the shoulder joint of the human body on a $B_X B_Y$ plane, a forearm connecting rod of the three-degree-of-freedom upper limb rehabilitation training robot responds to a rotation motion intention of the elbow joint of the human body on the $B_X B^Y$ plane; and the rocker of the three-degree-of-freedom upper limb rehabilitation training robot mainly responds to a rotation motion intention of the wrist joint on a $B_Y B_Z$ plane; an output signal of the six-dimensional force sensor comprises six-dimensional force data containing the three-dimensional force and the three-dimensional moment, wherein a force and a moment signal perpendicular to a motion plane are used to turn on/off the three-degree-of-freedom upper limb rehabilitation training robot by a patient, when the palm of the patient acts on the rocker, the force and the moment signal are generated accordingly, and then the robot is turned on; and when the robot needs to be turned off, the patient only needs to release the palm to stop the robot.

* * * * *